US011020531B2

(12) United States Patent
Ashmead et al.

(10) Patent No.: US 11,020,531 B2
(45) Date of Patent: Jun. 1, 2021

(54) SILICONE FREE DRUG DELIVERY DEVICES

(71) Applicant: W.L. Gore & Associates, Inc., Newark, DE (US)

(72) Inventors: Edgar G. Ashmead, Lincoln University, PA (US); Edward C. Gunzel, Oxford, PA (US); Michael Moritz, Media, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/591,688

(22) Filed: Oct. 3, 2019

(65) Prior Publication Data

US 2020/0061298 A1 Feb. 27, 2020

Related U.S. Application Data

(60) Division of application No. 15/425,082, filed on Feb. 6, 2017, now Pat. No. 10,471,212, which is a continuation-in-part of application No. 13/117,573, filed on May 27, 2011, now Pat. No. 9,597,458, which is a continuation-in-part of application No. 12/915,850, filed on Oct. 29, 2010, now Pat. No. 8,722,178.

(60) Provisional application No. 61/256,156, filed on Oct. 29, 2009.

(51) Int. Cl.
| | |
|---|---|
| *A61M 5/315* | (2006.01) |
| *A61K 38/48* | (2006.01) |
| *A61K 35/12* | (2015.01) |
| *A61M 5/32* | (2006.01) |
| *A61M 5/31* | (2006.01) |

(52) U.S. Cl.
CPC ......... *A61M 5/31513* (2013.01); *A61K 35/12* (2013.01); *A61K 38/4846* (2013.01); *A61M 5/3202* (2013.01); *A61M 2005/3118* (2013.01); *A61M 2005/3131* (2013.01); *A61M 2205/0238* (2013.01); *A61M 2207/00* (2013.01); *Y10T 156/1043* (2015.01); *Y10T 428/1321* (2015.01); *Y10T 428/1352* (2015.01); *Y10T 428/1359* (2015.01); *Y10T 428/1376* (2015.01); *Y10T 428/24992* (2015.01); *Y10T 428/3154* (2015.04)

(58) Field of Classification Search
CPC ............ A61M 5/31513; A61M 5/3202; A61M 2005/3131; A61M 2205/0238; A61K 38/4846; A61K 35/12
USPC ....................................................... 604/230
See application file for complete search history.

(56) References Cited

U.S. PATENT DOCUMENTS

| | | |
|---|---|---|
| 4,187,390 A | 2/1980 | Gore |
| 4,781,693 A | 11/1988 | Martinex |
| 4,964,866 A | 10/1990 | Szwarc |
| 5,009,646 A | 4/1991 | Sudo et al. |
| 5,112,664 A | 5/1992 | Waterland, III |
| 5,207,983 A | 5/1993 | Liebert et al. |
| 5,279,606 A | 1/1994 | Haber et al. |
| 5,374,473 A | 12/1994 | Knox |
| 5,397,628 A | 3/1995 | Crawley et al. |
| 5,431,310 A | 7/1995 | Kanner et al. |
| 5,596,814 A | 1/1997 | Zingle et al. |
| 5,879,789 A | 3/1999 | Dolan et al. |
| 6,016,848 A * | 1/2000 | Egres, Jr. ................. F16L 9/12 138/109 |
| 6,030,694 A | 2/2000 | Dolan et al. |
| 6,090,081 A * | 7/2000 | Sudo ................ A61M 5/31513 604/218 |
| 6,120,477 A | 9/2000 | Campbell |
| 6,331,351 B1 | 12/2001 | Walters et al. |
| 6,541,589 B1 | 4/2003 | Baillie |
| 6,645,635 B2 | 11/2003 | Muraki |
| 6,960,195 B2 | 11/2005 | Heinz et al. |
| 7,111,848 B2 | 9/2006 | Tachikawa et al. |
| 7,521,010 B2 | 4/2009 | Kennedy et al. |
| 8,722,178 B2 | 5/2014 | Ashmead et al. |
| 2003/0004491 A1 | 1/2003 | Tenhuisen et al. |
| 2004/0067705 A1 | 4/2004 | TonThat et al. |
| 2004/0084852 A1* | 5/2004 | Tachikawa ........ A61M 5/31513 277/534 |
| 2004/0157035 A1 | 8/2004 | Guizezetti et al. |

(Continued)

FOREIGN PATENT DOCUMENTS

| | | |
|---|---|---|
| CA | 2232617 | 3/1997 |
| CN | 1137319 | 12/1996 |

(Continued)

OTHER PUBLICATIONS

European Search Report dated Nov. 14, 2019 in corresponding EP 19179490.8.

(Continued)

*Primary Examiner* — Hui H Chin

(74) *Attorney, Agent, or Firm* — Amy L. Miller

(57) ABSTRACT

A pre-filled syringe having containing therein at least one therapeutic is provided. The syringe contains a silicone free barrel and an elastomeric syringe stopper that is covered with an expanded polytetrafluoroethylene barrier layer. The presence of a barrier layer that is at least partially porous on the outside of the syringe stopper improves the seal between the stopper and syringe barrel and minimizes the sliding force. In some embodiments, the barrel is formed of a glass material such as a borosilicate glass, that is free of silicone or other lubricants.

11 Claims, 10 Drawing Sheets

(56) References Cited

U.S. PATENT DOCUMENTS

| | | | |
|---|---|---|---|
| 2005/0070877 A1* | 3/2005 | Dobbie | A61K 31/683 604/506 |
| 2005/0074821 A1* | 4/2005 | Wild, Jr. | A61P 1/00 435/7.2 |
| 2008/0125710 A1 | 5/2008 | Hobson et al. | |
| 2009/0017007 A1* | 1/2009 | Andersen | A61K 33/30 424/94.64 |
| 2009/0093602 A1 | 4/2009 | Ford | |
| 2009/0169597 A1* | 7/2009 | Brown | A61P 19/04 424/423 |
| 2009/0196798 A1 | 8/2009 | Sassa et al. | |
| 2011/0137263 A1 | 6/2011 | Ashmead et al. | |
| 2011/0318596 A1 | 12/2011 | Elia et al. | |
| 2012/0251748 A1 | 10/2012 | Ashmead et al. | |
| 2012/0260607 A1 | 10/2012 | Moritiz | |

FOREIGN PATENT DOCUMENTS

| | | |
|---|---|---|
| EP | 0 375778 | 7/1990 |
| EP | 1 317 937 | 6/2003 |
| EP | 2374497 | 10/2011 |
| GB | 399336 | 10/1993 |
| JP | S6485665 | 3/1989 |
| JP | 2004305307 A | 9/1989 |
| JP | H01138454 | 9/1989 |
| JP | 08-206201 | 8/1996 |
| JP | H09507802 | 8/1997 |
| JP | 2001-104483 | 4/2001 |
| JP | 200286481 | 3/2002 |
| JP | 2004321614 | 11/2004 |
| JP | 2006288652 | 10/2006 |
| JP | WO2007/049332 | 5/2007 |
| JP | 2008154644 | 7/2008 |
| JP | WO2009011214 | 1/2009 |
| WO | WO94/02185 | 2/1994 |
| WO | WO94/13469 | 6/1994 |
| WO | WO99/17816 | 4/1999 |
| WO | WO01/60534 | 8/2001 |
| WO | WO03/095552 | 11/2003 |
| WO | WO2009/082034 | 7/2009 |
| WO | WO2011/059823 | 5/2011 |

OTHER PUBLICATIONS

Wattpad, Thermoplastic Elastomers, WP Technology, retrieved Jul. 15, 2013, 14 pages.

* cited by examiner

FIG 2A
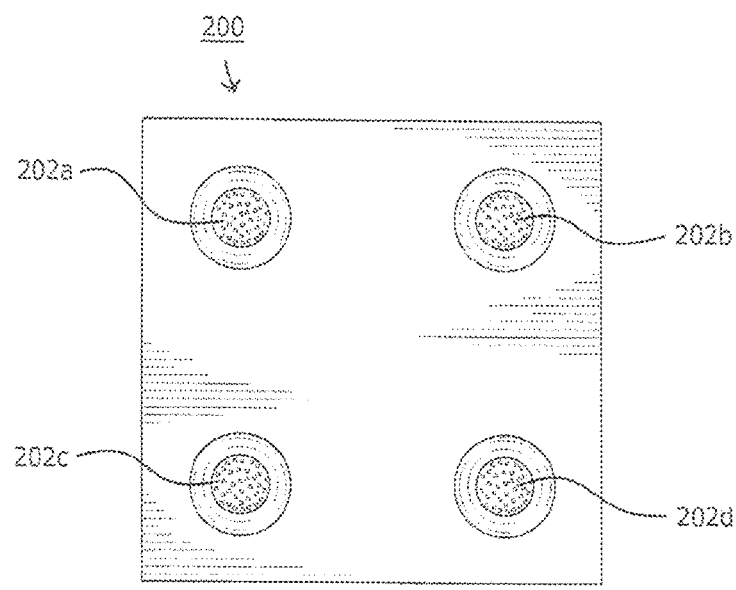
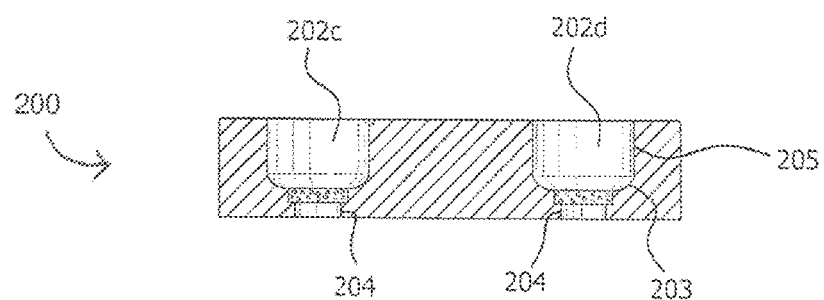
FIG. 2B

SILICONE FREE DRUG DELIVERY DEVICES

BACKGROUND

Syringes used for delivery of medicaments are principally constructed of a barrel and a stopper. The stopper is slidably fitted within the syringe barrel and may have a stopper rod affixed to it for actuation of the syringe and delivery of medicament. The stopper is generally constructed of an elastomer, with silicone oil applied. The silicone oil is applied to reduce sliding friction between the stopper and barrel and to improve the seal between them. The oil allows for ease of sliding when administering a dose which may ensure the full dose can be administered. Partial dosing is of particular concern in the case of pens and so-called auto injecting syringes. In such applications, the oil is also critical to prevent jamming of the device which can lead to trauma at the site of injection. The improved sealing provided by silicone oil also may ensure that no foreign contaminants like bacteria enter the syringe.

Recently there has developed a trend favoring pre-filled syringes which function to both store and deliver medicaments. Such pre-filled syringes may offer cost savings to the pharmaceutical industry and may improve safety, convenience and efficacy of medicament delivery. Biopharmaceuticals are an important class of pharmaceuticals that may increase the use of pre-filled syringes and related devices (pens, auto injectors and the like). Such biopharmaceuticals may include insulin, vaccines, antibodies, blood products, hormones, cytokines, and the like. As more pharmaceuticals and particularly biopharmaceuticals utilize delivery in pre-filled syringe and similar devices, the challenges of conventional syringe technology become apparent.

Several aspects of traditional syringe construction present a challenge for their use as pre-filled syringes. The use of silicone oil is a concern, because the oil may degrade the medicament and because a small amount of silicone may be injected with it. The oil may also be of particular concern with regard to biopharmaceuticals because it may cause aggregation of certain proteins.

Another issue that arises in prefilled syringes is that the elastomer of the stopper may contain leachable and extractable contaminants. These may also contaminate the medicament upon long term storage in syringes. Trace amounts of residual monomer or plasticizer or other impurities from the stopper can adversely affect the therapeutic or can have an adverse impact on the patient once injected.

Among the many other considerations affecting prefilled syringe devices and similar devices and their components are the need to be sterilized, stability with transport and storage for up to a few years, optical clarity, the need to integrate into existing filling equipment (including the durability requirements for stopper cleaning and insertion into the syringe barrel), leachables and extractables of all components of the syringe, and the need to maintain sterility from filling through administering of the contents, and finally user preferences and ergonomic considerations. For a variety of reasons the prefilled syringe market uses both glass and plastic barrels.

The foregoing considerations apply in similar manner to other containers, particularly containers suitable for medicaments. For example, rigid tip caps and other container closures as well as syringe barrels may benefit from barrier materials. In some such applications, the improved barrier material may serve as a barrier between the product contained in the container and the environment.

BRIEF DESCRIPTION OF THE DRAWINGS

FIG. 2A is a schematic illustration of the top view of a 4-cavity mold used in the thermoforming equipment of FIG. 1 in accordance with at least one embodiment;

FIG. 2B is a schematic illustration of the side view of a 4-cavity mold used in the thermoforming equipment of FIG. 1 in accordance with an embodiment;

DETAILED DESCRIPTION

Figure 1:
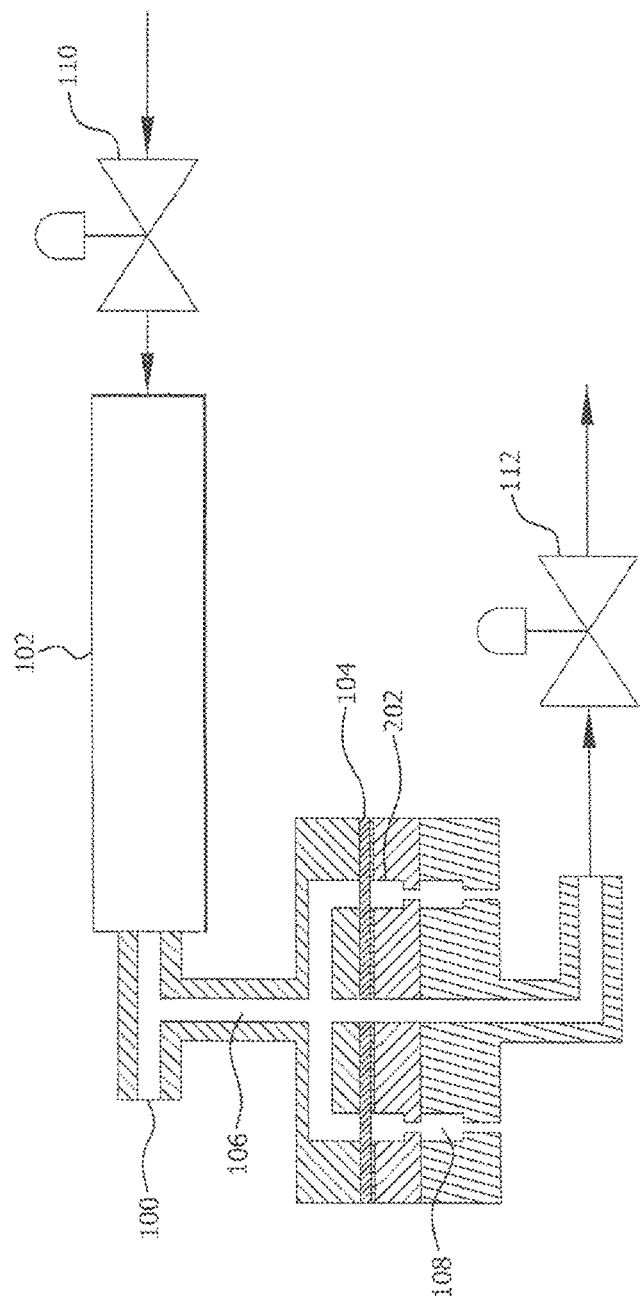
FIG. 1 is a schematic illustration of exemplary thermoforming equipment used to make most barrier film preforms in accordance with one or more embodiment.

The present invention provides a syringe stopper that is suitable for use in syringes without silicone oil or other liquid lubricants. In one aspect, the invention provides a low friction barrier between an elastomeric stopper material and a therapeutic in the syringe. The barrier may inhibit materials from leaching from the elastomer material or from extraction of compounds from medicants by the elastomer. A process is also described that allows for molding thin barrier layers while allowing adequate bonding with the elastomer. It is to be noted that the terms "stopper" and "syringe stopper" may be used interchangeably herein.

In another aspect, the inventive barrier material may also be used on non-elastomeric materials such as plastics (polypropylene, polycarbonate, polyethylene, etc.) thermoplastics, specifically fluoroplastic materials such as ethylene-perfluoro-ethlyene-propene (EFEP), polyvinylidene fluoride (PVDF), perfluoroalkoxy (PFA), and the like.

In certain embodiments, the invention may use barrier films including expanded fluoropolymer films and, particularly expanded polytetrafluoroethylene films. Barrier films based on expanded polytetrafluoroethylene (ePTFE) can provide for thin and strong barrier layers to leachables and extractables. The superior strength of the expanded fluoropolymer structure allows these materials to form thin barriers which remain intact during the forming process and installation of the stopper into the syringe body.

The use of at least partially porous and advantageously fibrilizing materials, such as expanded polytetrafluoroethylene (ePTFE) in combination with barrier materials may provide many advantages. In one aspect, the use of such partially porous materials may provide a scaffold that enables thin strong barrier layers to be made and improves the bond between the elastomer and the barrier. Barrier compliance is critical to maintaining a seal between the stopper and the barrel; porous materials may also provide for improved compliance of the stopper. Improved compliance may result from reduced film thickness, flexural compliance, or the compressibility of one or more layers of the porous material. Accordingly, by providing a barrier that is at least partially porous to the outside of the syringe stopper, the seal between the stopper and syringe barrel may be improved while the sliding force is minimized. In addition the present disclosure enables the elimination of silicone (e.g., silicone oil) from syringe barrels, therefore enabling a significant reduction in both visible and sub-visible particles.

The barriers may be of single layer or multiple layer construction. As described herein, layers may be described functionally. However, the functional names of the various layers in the descriptions of embodiments that follow may not describe all of the potential functions of any given layer. Accordingly, it will be understood that such functional nomenclature is not intended to be limiting of any layer property. For example, a barrier layer may have additional properties and functions such as providing a low friction surface, increasing bond strength and the like. Moreover, in multi-layer embodiments, each layer may contribute to the reduction of leachable and extractable materials regardless of its designation as a barrier layer or otherwise.

Figure 5:
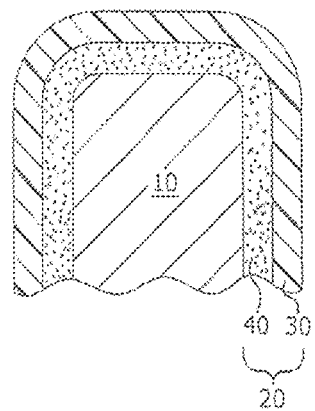
FIG. 5 is a cross sectional illustration of a syringe stopper according to one embodiment.

FIG. 5 shows a first embodiment of syringe stopper of the current invention comprised of an elastomer body 10, and a fluoropolymer barrier 20. The elastomer body 10 can be comprised of any elastomer suitable for the application, most notably rubbers constructed butyl, bromobutyl, chlorobutyl, silicone, nitrile, styrene butadiene, polychloroprene, ethylene propylene diene, fluoroelastomers, or blends of any of the foregoing. The materials of the barrier 20 are chosen to provide low coefficient of friction, compliance, low extractables and leachables, good barrier properties as they relate to extractables and leachables from the elastomer body.

Figure 8:
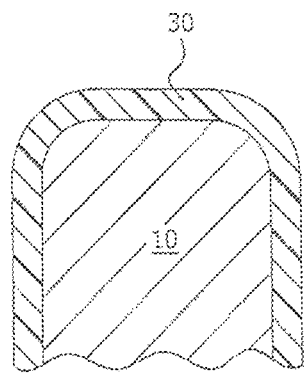
FIG. 8 is a cross-sectional illustration of a syringe stopper in accordance with at least one embodiment.

In an embodiment, the barrier 20 may comprise a single layer of densified ePTFE. FIG. 8 shows a syringe stopper of the current invention comprised of an elastomer body 10 and a barrier layer 30. The elastomer body may comprise any of these previously mentioned materials. In this aspect, the barrier film may comprise densified expanded fluoropolymer, preferably densified ePTFE.

A densified ePTFE film may be obtained in the manner described in U.S. Pat. No. 7,521,010 to Kennedy, et al. The densified ePTFE film is then combined with an elastomer to construct a syringe stopper. In this embodiment, the densified ePTFE film is thermoformed to make a preform. Thermoforming is done at process temperatures sufficiently above the nodal melt to ensure melt forming while preserving barrier and strength properties. The high strength expanded film allows for forming extremely thin barrier films. Barrier films can be made with thicknesses ranging from 0.5 micron to 20 microns. The films are preferentially less than 30 microns. The film can optionally be pre-treated or post treated with chemical etching, plasma treating, corona, roughening or the like to improve bonding to the elastomer body.

The thermoformed, densified ePTFE preform can be combined with the elastomer body by injection molding, compression molding, priming and post laminating around an elastomer perform, or other suitable means. Examples of elastomers that can be used to form the elastomer body include silicone, butyl, nitrile, polyurethane, fluoroelastomers, styrene ethylene butadiene styrene elastomers, styrene butadiene rubbers, and the like.

In another embodiment, the barrier 20 may comprise a composite fluoropolymer film having a barrier layer 30 and a porous layer 40. The barrier layer 30 can be comprised of densified expanded polytetrafluoroethylene (ePTFE), polytetrafluoroethylene (PTFE), fluorinated ethylene propylene (FEP), polyethylene, polypropylene, polyvinylidene fluoride, polyvinylfluoride, perfluoropropylevinylether, perfluoroalkoxy polymers, and the like. The porous layer 40 can be comprised of ePTFE or other porous expanded and advantageously fibrillizing fluoropolymers (for example, ePTFE as taught in U.S. Pat. No. 6,541,589). The ePTFE layers may advantageously be filled with an organic or inorganic material to provide color lubricity or other function.

In one or more embodiment, the barrier layer 30 may include, or be formed of, one or more of the following materials: ultra-high molecular weight polyethylene as taught in U.S. Patent Publication No. 2014/0212612 to Sbriglia; polyparaxylylene as taught in U.S. patent application Ser. No. 14/810,999 to Sbriglia; polylactic acid as taught in U.S. patent application Ser. No. 14/811,054 to Sbriglia, et al.; and/or VDF-co-(TFE or TrFE) polymers as taught in U.S. patent application Ser. No. 14/811,100 to Sbriglia.

In another embodiment a barrier is constructed by coating or otherwise depositing a barrier polymer onto the porous expanded layer to create a composite film. One such example of this would be to deposit granular or powdered fluoropolymers such as powdered PTFE onto the porous ePTFE surface in a coating process. The ePTFE support should be constructed to be thermally stable enough to allow heat treatment of the deposited fluoropolymer for the creation of a barrier or for bonding of the deposited layer to the porous ePTFE support.

Figure 6:
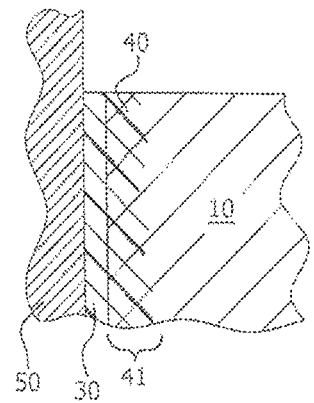
FIG. 6 is a cross sectional illustration of a syringe stopper according to another embodiment.

In certain embodiments, elastomer material may advantageously penetrate the porous structure of the barrier. FIG. 6 shows a cross-section of a stopper according to an embodiment depicting the syringe barrel wall 50 the barrier film 30 the porous layer 40 and the elastomer body 10. Specifically, FIG. 6 shows a region of partial penetration 41 of the elastomer material into the porous structure 40. Penetration of the elastomer material into the porous structure may improve the bond between elastomer and barrier.

Figure 7:
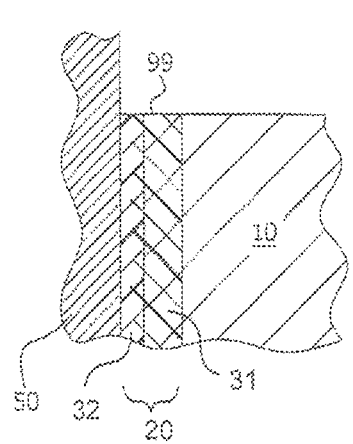
FIG. 7 is a cross sectional illustration of a syringe stopper according to another embodiment.

FIG. 7 shows a cross-section of another embodiment of a syringe stopper according to the invention including the syringe barrel wall 50, a barrier 20, and an elastomer body 10. The barrier is comprised of a barrier layer 32, and a porous layer 31. In this embodiment, the barrier layer 32 comprises a coating deposited onto the porous layer 31. The barrier layer may comprise a polymer at least partially imbibed into the porous layer 31 in a manner that creates a porous layer composite section 99. This porous layer composite section 99 may improve bonding of the barrier polymer to the porous layer. The porous composite section 99 may also provide support for the barrier polymer to impart strength, toughness, compliance and stability which may be beneficial in both the forming process and in the application.

In an aspect, the barrier layer 32 may comprise an imbibed barrier polymer applied in a manner that allows leaves certain sections the porous layer exposed on the surface. In this aspect the porous layer may be sufficiently exposed to allow the exposed sections to come in contact with the syringe wall 50. In this aspect, the porous polymer is advantageously comprised of ePTFE or other suitable lubricious, expanded porous fluoropolymer. The exposed sections of fluoropolymer may reduce the coefficient of friction of the barrier film against the wall.

Figure 9:
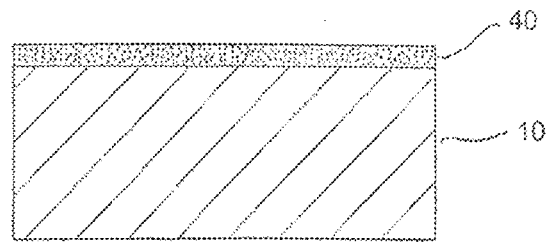
FIG. 9 is a cross-sectional illustration of a syringe stopper in accordance with an embodiment.
Figure 10A:
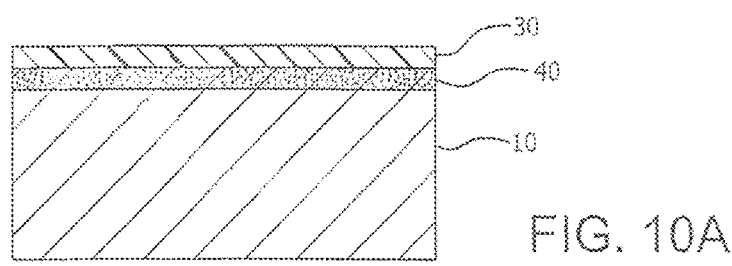
FIG. 10A is a cross-sectional illustration of a syringe stopper in accordance with an embodiment.
Figure 10B:
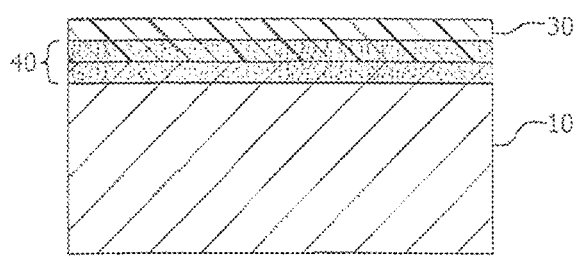
FIG. 10B is a cross-sectional illustration of a syringe stopper in accordance with at least one embodiment.

In many of the embodiments of the invention, a porous layer is disposed between the barrier layer surface and the elastomer of the stopper. The inventive stopper may advantageously include various degrees of penetration of either elastomer material or barrier polymer into the porous material as shown in FIGS. 9 through 13. FIG. 9 is a cross-sectional view of a stopper showing an elastomeric layer 10 and a porous layer (ePTFE layer). FIG. 10A is a cross-sectional view of the stopper showing the elastomer layer 10 and a composite layer comprising a fluoropolymeric barrier layer 30 and a porous ePTFE layer 40. In the embodiment depicted in FIG. 10A, the elastomeric material from layer 10 substantially fills the pores of the ePTFE layer 40.

Figure 11:
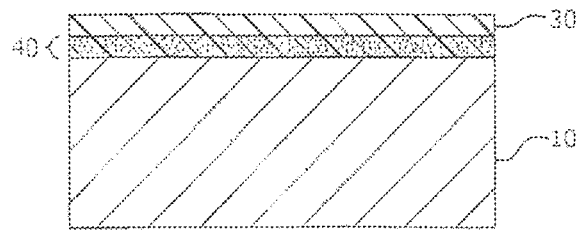
FIG. 11 is a cross-sectional illustration of a syringe stopper in accordance with an embodiment.
Figure 12:
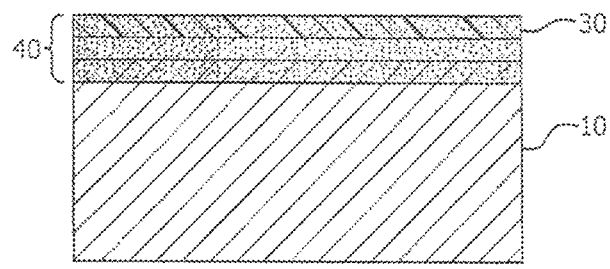
FIG. 12 represents a cross-sectional illustration of a syringe stopper in accordance with an embodiment.
Figure 13:
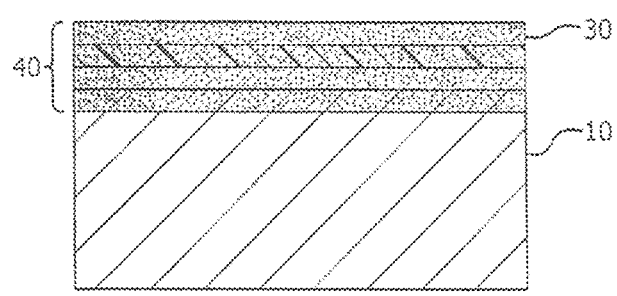
FIG. 13 represents a cross-sectional illustration of a syringe stopper in accordance with an embodiment.

Alternatively, the barrier polymer 30 may substantially fill the porous structure 40, as shown in FIG. 11. In another aspect, the porous material 40 is filled to a substantially similar degree with barrier polymer 30 and elastomer 10, leaving few open pores in the porous structure as in FIG. 10B. In still another aspect, both the barrier polymer and the elastomer partially fill the porous structure, while leaving some open pores between them as shown in FIG. 12. Other variations of penetration of elastomer and or barrier fluoropolymer may be readily apparent, one such variant shown in FIG. 13. Each may have advantages according to the specific application, with due consideration to the various desirable characteristics of the finished device, such as reduced friction, improved barrier properties, and improved sealing. The degree of penetration of either barrier polymer or elastomer may be controlled by any means known, but include variations in time, temperature, pressure, and porosity of the porous material. In one aspect the porous material may, for example have a porosity that varies with depth.

In still another embodiment, the barrier may comprise a composite of a densified ePTFE film and a thin layer of porous ePTFE bonded to the barrier layer film. A densified ePTFE film may be obtained as described in U.S. Pat. No. 7,521,010 to Kennedy et al. The ePTFE/densified ePTFE composite may be combined in the manner described in U.S. Pat. No. 6,030,694 to Dolan, et al.

In this embodiment, a composite barrier comprises a layer of densified ePTFE film and a porous ePTFE layer. The porous ePTFE layer is constructed in a manner that it retains most of its porosity through thermoforming. It is also sufficiently compliant that it improves sealability against the syringe barrel wall. To accomplish this, at least a portion of the porous layer may remain sufficiently open after thermoforming and post compression molding with the elastomer. This open porosity allows some compressibility which may aid in the conformability and seal of the stopper to the surface.

The thickness of the densified ePTFE film would be suitably tailored to the application with pre-thermoform thicknesses of less than 100 microns, more preferably, less than 50 microns, more preferably less than 30 microns. Additionally, the flexural rigidity of the composite film would need to be suitably tailored to ensure compliance and sealability while retaining sufficient strength for this application.

The ePTFE porous layer would be preferably less than 150 microns thick. To improve performance as a bonding layer, the ePTFE porous layer should be made sufficiently open to allow for at least partial penetration of the elastomer into the porous (i.e. and fibrillated structure onto the surface of the nodes or fibrils) during elastomer forming.

To construct the barrier preform, the composite barrier may be thermoformed at temperatures, rates and pressures suitable to allow the densified film to form to the shape of the female cavity of a stopper mold. The more porous ePTFE layer may be oriented toward the inside of the mold cavity, while the densified ePTFE barrier layer will be oriented toward the outer wall of the mold. The thermoforming can be done at temperature ranges suitable to form the ePTFE based film, without fracturing or otherwise disturbing the barrier provided by the densified ePTFE barrier layer. Suitable temperatures could be in the range of 330-400° C., more preferably 350-380° C. at pressures suitable to form without fracturing the barrier layer, or substantially collapsing the porous layer.

The thermoformed barrier preform may be integrated with an elastomeric syringe stopper of the current invention by, for example, by injection molding or compression molding an elastomer like butyl rubber or silicone or Viton® (a fluoroelastomer). The porous ePTFE layer can be advantageously made stable to the elastomer injection or compression molding process, thereby maintaining some of its porous structure. The porous structure may improve the bond of the elastomer to the barrier. This may result in improved compliance for sealability, as the porous layer allows for some compressibility for better, low force sealing.

In yet another embodiment, a barrier can be made by forming a thin densified composite comprising a porous ePTFE layer and a thermoplastic barrier layer. In this aspect, a thermoplastic having a surface with a low coefficient of friction is preferred. Accordingly, fluoropolymer based thermoplastics such as FEP, PFA, THV may be applicable. A barrier according to this aspect may be an FEP/ePTFE laminate obtained by following the process taught in WO 94/13469 to Bacino. The barrier may be formed at process temperatures above the softening temperature or even above the melt of the FEP film in a female cavity mold.

The composite barrier of ePTFE and FEP described herein may allow forming of surprisingly thin, strong barrier films. In one embodiment, the ePTFE layer may act as a support during shape forming to allow thin barrier films. The porous ePTFE layer may also act as a reinforcement to the thermoplastic layer to maintain film strength and integrity of the barrier layer as described above, the ePTFE porous layer can also serve as a bonding layer when a portion of the ePTFE is allowed to remain porous and oriented toward the inside of the mold.

Subsequent combination of a composite film with an elastomer through, for example, compression molding can allow the porous portion of the ePTFE to be adhered to by partial penetration of the elastomer into the porous structure. Alternatively, if the ePTFE/FEP composite barrier is fully imbibed in a manner that leaves no residual porosity in the composite film, the composite barrier film can be chemically modified by etching or plasma or physically modified by roughening, for example, to allow bonding to the elastomer. In another aspect, the ePTFE porous layer can be comprised of multiple layers of ePTFE, each having varying pore size and structure. This multi-layer construction may facilitate control of the degree imbibing of the barrier polymer or the elastomer or to allow other desired properties.

One surprising element of some embodiments of the current invention is that the porous film portion of the expanded fluoropolymer layer can maintain its structure through thermoforming and post injection or compression molding of the elastomer. This allows for some of the advantages described above including improved compliance and sealability as well as improved bond between the barrier film and the elastomer body.

In another embodiment, a composite barrier is made by laminating an ePTFE porous layer to a densified ePTFE barrier layer using a thin layer of an adhesive, e.g., a fluoropolymer thermoplastic such as perfluoroakoxy (PFA). In this embodiment, a syringe stopper may be made by combining the composite barrier with an elastomer layer such that the thermoplastic polymer bonds the densified ePTFE barrier layer and the porous ePTFE layer together. The ePTFE porous layer of the composite barrier is bonded to the elastomer (i.e. stopper material) during the molding process.

A composite film may be made by starting with a multi-layer porous expanded fluoropolymer film and substantially densifying one or more of the porous layers. In one embodiment, the porous layer may be densified by application of pressure during the molding or syringe insertion process.

In another embodiment, a porous expanded fluoropolymer film may be formed and then post applied to create a barrier layer. For instance, this could be accomplished by choosing an ePTFE film of suitable deformation characteristics that it allows for deformation into the mold at relatively low temperatures (e.g., less than 200° C.). A suitable ePTFE film might have, for instance, tensile properties demonstrating high elongation or low modulus at the deformation temperature. The ePTFE film can be formed into the female mold cavity through a variety of means including through the use of air pressure, through the use of a male mold form, or other suitable means to allow forming of the ePTFE.

One method would be to form a deformable ePTFE film during the injection or compression molding process. This would allow for a structure wherein the ePTFE comprised the outermost layer of the syringe stopper. The pore structure, thickness, and other properties can be suitably tailored to allow controlled penetration of the elastomer into the expanded fluoropolymer layer. In one embodiment, the elastomer is allowed to penetrate through the expanded fluoropolymer film, allowing for a composite structure of expanded fluoropolymer film and elastomer at the outer surface. If the outer surface is suitably dense and nodal, it can allow for a significant reduction in friction relative to the elastomer itself. In one exemplary embodiment, a stopper is created using the aforementioned process of forming an ePTFE film in a female mold and post-laminating, imbibing or coating a barrier onto the outermost surface of the ePTFE film. In the coating and imbibing processes, the ePTFE can be used to control the barrier thickness.

A syringe stopper of the current embodiment may include a composite barrier having multiple porous layers or multiple barrier layers or both. The properties of a composite barrier so constructed can be more suitably tailored to allow optimal compliance through the properties of the thin films while providing low surface friction against the barrel and adequate barrier properties to leachables, extractables and gas permeation.

Another way of making an ePTFE syringe stopper with a porous outer layer and creating a barrier layer may be to post densify the ePTFE with pressure and temperature. It is to be appreciated that there are many variations of the processes described herein could be utilized without departing from the scope of the disclosure.

Any of the ePTFE fluoropolymers used in syringe stopper of the current invention may be made with an expanded fluoropolymer film such as PTFE, modified PTFE, and PTFE and tetrafluoroethylene (TFE) copolymers such as, for example, the resins as described in U.S. Pat. No. 6,541,589 and U.S. Patent Publication No. 2009/0093602.

There are also a wide variety of processes for forming the film and attaching it to the elastomer body which may be utilized without departing from the invention. In addition to what is described above, one could form an ePTFE film at low temperatures.

The stoppers described herein may be used in syringes for storing and delivering a fluid, typically for medical use. In some embodiments, the syringe is pre-filled with a therapeutic (e.g., a pre-filled syringe). In one embodiment, the syringes contain a therapeutic that treats diseases, such as ocular disease (e.g., macular degeneration and glaucoma). Advantageously, the syringes do not contain a lubricant such as silicone or silicone oil or other liquid lubricant. Thus, the barrels in the syringes described herein are free of silicone and silicone oil (or other liquid lubricant).

Figure 18:
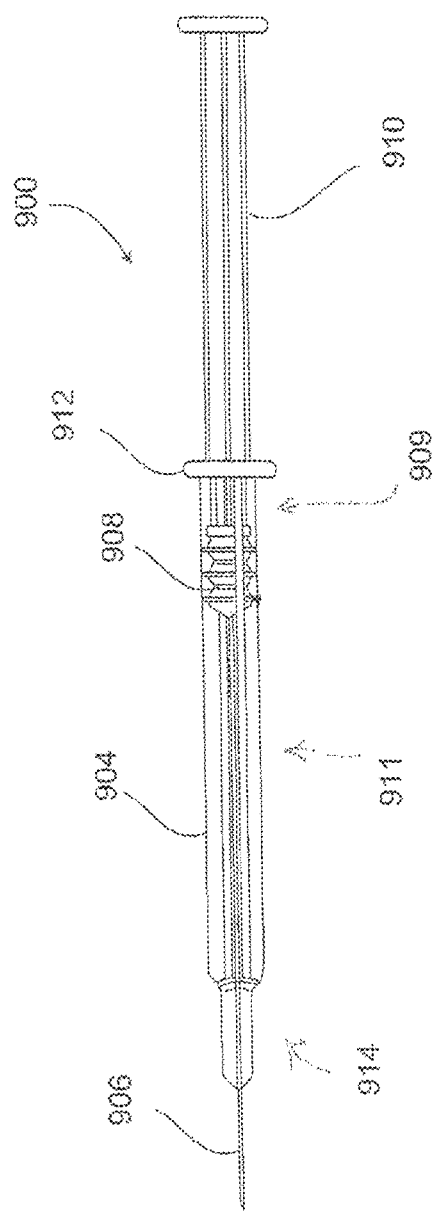
FIG. 18 is a schematic illustration of an exemplary syringe according to one embodiment.

Referring to FIG. 18, an exemplary syringe 900 is depicted that includes a plunger 910 with a stopper 908 that is slidably disposed within a barrel 904 for storing and dispensing a fluid (not shown), such as a therapeutic, from a needle 906. The stopper 908 can be moved from a proximal end to a distal end of the barrel 904 to deliver the fluid contained therein. A sliding surface having a slide force is created between the stopper 908 and the barrel 904. In exemplary embodiments, the slide force between the stopper 908 and the barrel 904 may be less than 15 N, less than 10 N, or less than 5 N. The syringe 900 may be used to store and/or deliver a medical fluid, such as a pharmaceutical composition or a biological substance, into a patient. Alternatively, the syringe 900 may be used to obtain fluids from a patient, such as, for example, a blood sample.

The barrel 904 is a tubular body having an outer diameter and an inner diameter. The proximal end 909 of the barrel 904 may have flanges 912 that radially extend away from the exterior surface of the barrel 904 for convenient gripping during use. The barrel 904 may be formed of a substantially rigid or hard material, such as a glass material (e.g., a borosilicate glass), a ceramic material, one or more polymeric materials (e.g., polypropylene, polyethylene and copolymers thereof), a metallic material, a plastic material (e.g. cyclic olefin polymers (COC) and cyclic olefin copolymers (COP)), and combinations thereof. The inner diameter of the barrel 904 at the proximal end 909 and middle portion 911 may be generally constant. Near the distal end 914, the inner and outer diameters of the barrel 904 may be tapered to smaller diameters to facilitate the connection of the needle 906 and the barrel 904.

In some embodiments, the distal end 114 of the barrel 104 includes a luer connector (not illustrated), e.g., a luer-lock fitting. The luer connector can be configured to receive needle tip components such that several different needle sizes can be interchangeably used with a single barrel 904 in a syringe 900. Alternatively, a luer connector can be utilized in place of a needle in a needless system.

In another aspect, the invention provides an improved tip cap for a syringe. A tip cap may be provided as a protective covering to a syringe needle. Accordingly, a tip cap may provide a seal to the end of the needle to prevent contamination of a medicament. As with a syringe stopper, a tip cap construction that minimizes leachable and extractable components is desirable. Moreover, the tip cap must be readily removable. Moderate friction between the tip cap and needle is preferred. The tip cap according to the present invention therefore may be of construction similar to that of the syringe stopper. In contrast to the stopper, however, the barrier layer is positioned in the tip cap to be adjacent to the needle on final assembly. As the challenges between tip cap and stopper are similar, each of the constructions described herein with regard to stoppers may be adapted for use in a tip cap construction.

In another aspect, the invention provides an internal barrier layer for a container. The container may be of a material without barrier properties. The addition of a barrier layer to the inside surface of the container may improve barrier properties of the container. The container may be made of any material, including thermoset material, thermoplastic material, metal, ceramic or glass.

The container may be formed of a variety of materials. Advantageously, the container is selected from materials that will form a bond with the barrier layer. In one aspect, the container is advantageously formed from thermoplastic material. The container constructed of thermoplastic may be formed separately or simultaneously with the barrier layer. Preferably, the barrier layer is pre formed to a shape approximating the inside of the container. The container and the preform may be placed together into a mold and formed under appropriate heat and pressure to the final shape of the container with barrier layer. In this aspect the barrier layer may form a strong bond with the thermoplastic of the container during the final molding process.

In another aspect, the container may be a thermoset plastic. Thermoset plastics may be injected into the mold at the time of final molding of the barrier or barrier composite perform. In another aspect, the thermoset plastic may be formed or made by other means separately from the perform. In this aspect, the container of the thermoset plastic may function as the mold, and the barrier layer or composite barrier layer maybe molded to the thermoset material.

The barrier may be selected from a number of combinations described herein. In one embodiment, the barrier is a composite of a densified expanded fluoropolymer, such as ePTFE. The densified, expanded fluoropolymer may include copolymers of ePTFE. The densified expanded fluoropolymer may be combined with a thermoplastic such as FEP or EFEP to form a barrier composite.

During the molding process, additional layers may be added to the barrier layer or composite barrier layer to construct a container or to improve bonding of barrier or barrier composite to the container. For example thermoplastic layers may be added to improve bonding to a thermoplastic container. In one embodiment PVDF sheet may be added to the molding process. The PVDF layer may add some rigidity to a thermoplastic container. In some embodiments, a relatively thick thermoplastic film may be formed in the mold to make the container. In another embodiment, a porous ePTFE film may be added between the thermoplastic layers to improve bonding between them.

The syringes, tip caps, and other embodiments of the present disclosure may be used in combination with different therapeutic compounds including, but not limited to, drugs and biologics such as Coagulation Factors, Cytokines, Epigenetic protein families, Growth Factors, Hormones, Peptides, Signal Transduction molecules, and mutations thereof; also including Amino Acids, Vaccines and/or combinations thereof. Therapeutic compounds further include antibodies, antisense, RNA interference made to the above biologics and their target receptors and mutations of thereof. Additional therapeutic compounds include Gene Therapy, Primary and Embryonic Stem Cells. Also included in the therapeutic compounds are antibodies, antisense, RNA interference to Protein Kinases, Esterases, Phosphatases, Ion channels, Proteases, structural proteins, membrane transport proteins, nuclear hormone receptors and/or combinations thereof. Additionally it is to be understood that at least one of the therapeutic compounds identified herein used in the instant disclosure, also two or more therapeutic compounds listed in this application are considered to be within the purview of the present disclosure.

Examples of Coagulation Factors include, but are not limited to: Fibrinogen, Prothrombin, Factor I, Factor V, Factor X, Factor VII, Factor VIII, Factor XI, Factor XIII, Protein C, Platelets, Thromboplastin, and Co-factor of Vila.

Examples of Cytokines include, but are not limited to: Lymphokines, Interleukins, Chemokines, Monokines, Interferons, and Colony stimulating factors.

Examples of Epigenetic protein families include, but are not limited to: ATPase family AAA domain-containing protein 2 (ATAD2A), ATPase family-AAA domain containing 2B (ATAD2B), ATPase family AAA domain containing-2B (ATAD2B), bromodomain adjacent to zinc finger domain-1A (BAZ1A), bromodomain adjacent to zinc finger domain-1B (BAZ1B), bromodomain adjacent to zinc finger domain-2A (BAZ2A), bromodomain adjacent to zinc finger domain-2A (BAZ2A), bromodomain adjacent to zinc finger domain-2B (BAZ2B), bromodomain-containing protein 1 (BRD1), Bromodomain containing protein 2-1st bromodomain (BRD2), Bromodomain containing protein 2-1st & 2nd bromodomains (BRD2), bromodomain-containing protein 2 isoform 1-bromodomain 2 (BRD2(2)), bromodomain-containing protein 3-bromodomain 1 (BRD3(1)), Bromodomain-containing protein 3-1st bromodomain (BRD3), Bromodomain-containing protein 3-1st & 2nd bromodomains (BRD3), bromodomain-containing protein 3-bromodomain 2 (BRD3(2)), Bromodomain containing protein 4-1st bromodomain (BRD4), bromodomain-containing protein 4 isoform long-bromodomains 1 and 2 (BRD4(1-2)), bromodomain-containing protein 4 isoform long-bromodomain 2 (BRD4(2)), bromodomain-containing protein 4 isoform short (BRD4(full-length-short-iso.)), Bromodomain containing protein 7 (BRD7), bromodomain containing 8-bromodomain 1 (BRD8(1)), bromodomain containing 8-bromodomain 2 (BRD8(2)), bromodomain-containing protein 9 isoform 1 (BRD9), Bromodomain containing testis-specific-1st bromodomain (BRDT), Bromodomain containing testis-specific-1st & 2nd bromodomains (BRDT), bromodomain testis-specific protein isoform b-bromodomain 2 (BRDT (2)), bromodomain and PHD finger containing-1 (BRPF1), bromodomain and PHD finger containing-3 (BRPF3), bromodomain and PHD finger containing-3 (BRPF3), Bromodomain and WD repeat-containing 3-2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase-KAT2A (GCN5L2), Euchromatic histone-lysine N-methyltransferase 1 (EHMT1), Histone-lysine N-methyltransferase MLL (MLL), Polybromo 1-1st bromodomain (PB1(1)), Polybromo 1-2nd bromodomain (PB1(2)), polybromo 1-bromodomain 2 (PBRM1(2)), polybromo 1-bromodomain 5 (PBRM1(5)), Histone acetyltransferase KAT2B (PCAF), PH-interacting protein-1st bromodomain (PHIP(1)), PH-interacting protein-2nd bromodomain (PHIP(2)), Protein kinase C-binding protein 1 (PRKCBP1), Protein arginine N-methyltransferase 3 (PRMT3), SWI/SNF related-matrix associated-actin dependent regulator of chromatin-subfamily a-member 2 (SMARCA2), SWI/SNF related-matrix associated-actin dependent regulator of chromatin-subfamily a-member 4 (SMARCA4), Nuclear body protein-SP110 (SP110), Nuclear body protein-SP140 (SP140), Transcription initiation factor TFIID subunit 1 (TAF1(1-2)), TAF1 RNA polymerase II-TATA box binding protein (TBP)-associated factor-250 kDa-bromodomain 2 (TAF1(2)), Transcription initiation factor TFIID subunit 1-like-1st bromodomain (TAF1L(1)), Transcription initiation factor TFIID subunit 1-like-2nd bromodomain (TAF1L(2)), tripartite motif containing 24 (TRIM24(Bromo.)), tripartite motif containing 24 (TRIM24(PHD-Bromo.)), E3 ubiquitin-protein ligase TRIM33 (TRIM33), tripartite motif containing 33 (TRIM33(PHD-Bromo.)), WD repeat 9-1st bromodomain (WDR9(1)), and WD repeat 9-2nd bromodomain (WDR9(2)).

Examples of growth factors include, but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), bone morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), and Insulin-like growth factors.

Examples of Hormones include, but are not limited to: Amino acid derived (such as melatonin and thyroxine), Thyrotropin-releasing hormone, Vasopressin, Insulin, Growth Hormones, Glycoprotein Hormones, Luteinizing Hormone, Follicle-stimulating Hormone, Thyroid-stimulating hormone, Eicosanoids, Arachidonic acid, Lipoxins, Prostaglandins., Steroid, Estrogens, Testosterone, Cortisol, and Progestogens.

Examples of Proteins and Peptides and Signal Transduction molecules include, but are not limited to: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-terminal-binding protein 1, Structural maintenance of chromosomes protein 1A, Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), and Catenin beta 1 (cadherin-associated protein or CTNNB1).

Examples of G Protein-Coupled Receptors (GPCR) include, but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C-C motif) receptor family, Sphingosine 1-phosphate receptor family, Succinic receptor, Cholinergic receptor family. Chemokine-like receptor family, Cannabinoid receptor family, Corticotropin releasing hormone receptor family, prostaglandin D2 receptor, Chemokine C-X3-C receptor family, Chemokine (C-X-C motif) receptor family, Burkitt lymphoma receptor, Chemokine (C-X-C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin I2 (prostacyclin) receptor family, Parathyroid hormone receptor family, muscarinic acetylcholine receptors (such as rM4), Prostanoid DP2 receptor (rGPR44), Prokineticin receptor family, Relaxin family peptide receptor family, Secretin receptor (secretin), Frizzled class receptor (Smoothened), trace amine associated receptor family, Tachykinin family, Thromboxane A2 receptor (TP), Thyrotropin-releasing hormone receptor (TRH1), and Thyroid Stimulating Hormone Receptor (TSH).

Examples of nuclear hormone receptors include, but are not limited to: Androgen receptor (AR), Estrogen related receptor alpha (ESRRA), Estrogen receptor 1 (ESR1), Nuclear receptor subfamily 1-group H-member 4 (NR1H4), Nuclear receptor subfamily 3-group C-member 1 (glucocorticoid receptor) (NR3C1), Nuclear receptor subfamily 1-group H-member 3 (Liver X receptor α) (NR1H3), Nuclear receptor subfamily 1-group H-member 2 (Liver X receptor β) (NR1H2), Nuclear receptor subfamily 1-group H-member 2 (Liver X receptor β) (NR1H2), Nuclear receptor subfamily 3-group C-member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor α (PGR), Progesterone receptor β (PGR), Retinoic acid receptor-alpha (RARA), Retinoic acid receptor-beta (RARB), Retinoid X receptor-alpha (RXRA), Retinoid X receptor-gamma (RXRG), Thyroid hormone receptor-alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, and Nerve growth factor-induced-B, Germ cell nuclear factor.

Examples of membrane transport proteins include, but are not limited to: ATP-binding cassette (ABC) superfamily, solute carrier (SLC) superfamily, multidrug resistance protein 1 (P-glycoprotein), organic anion transporter 1, and and proteins such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STLN2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, and OATP2A1.

Examples of structural proteins include, but are not limited to: tubulin, heat shock protein, Microtubule-stabilizing proteins, Oncoprotein 18, stathmin, kinesin-8 and kinesin-14 family, Kip3, and Kif18A.

Examples of proteases include, but are not limited to ADAM (a disintegrin and metalloprotease) family.

Examples of Protein kinases include, but are not limited to: AP2 associated kinase, Homo sapiens ABL proto-oncogene 1-non-receptor tyrosine-protein kinase family, c-abl oncogene 1 receptor tyrosine kinase family, v-abl Abelson murine leukemia viral oncogene homolog 2, activin A receptor family, chaperone-ABC1 activity of bc1 complex homolog (S. pombe) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family-SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (S. pombe) (CHEK1), CHK2 checkpoint homolog (S. pombe) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family-Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoietic cell kinase (HCK), homeodomain interacting protein kinase family, mitogen-activated protein kinase kinase kinase family, hormonally up-regulated Neu-associated kinase (HUNK), intestinal cell (MAK-like) kinase (ICK), Insulin-like growth factor 1 receptor (IGF1R), conserved helix-loop-helix ubiquitous kinase (IKK-alpha), inhibitor of kappa light polypeptide gene enhancer in B-cells-kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/threonine kinase family leucine-rich repeat kinase family, v-yes-1 Yamaguchi sarcoma viral related oncogene homolog (LYN), male germ cell-associated kinase (MAK); MAP/microtubule affinity-regulating kinase family such as microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4, 5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family; Spleen tyrosine kinase (SYK) such as TAO kinase family; TANK-binding kinase 1 (TBK1) such as tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), and zeta-chain (TCR) associated protein kinase 70 kDa (ZAP70).

Cell therapy using cells that are derived primarily from: endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands and urogenital tract), Extracellular matrix cells, Contractile cells, Blood and immune system cells, Germ cells, Nurse cell, Interstitial cells and combinations thereof. Additionally in the scope of the invention are cells that are genetically, chemically or physically altered or otherwise modified.

Examples of Exocrine secretory epithelial cells include but are not limited to: Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II pneumocyte of lung, and Clara cell of lung; Hormone-secreting cells including, but not limited to: Anterior pituitary cells, Intermediate pituitary cell, Magnocellular neurosecretory cells, Gut and respiratory tract cells, Thyroid gland cells, Parathyroid gland cells, Adrenal gland cells, Leydig cell of testes secreting testosterone, Theca interna cell of ovarian follicle secreting estrogen, Corpus luteum cell of ruptured ovarian follicle secreting progesterone, Juxtaglomerular cell, Macula densa cell of kidney, Peripolar cell of kidney, Mesangial cell of kidney, and Pancreatic islets; Keratinizing epithelial cells including, but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, and Hair matrix cell; Wet stratified barrier epithelial cells including, but not limited to: Surface epithelial cell of stratified squamous epithelium and basal cell of epithelia of cornea, tongue, oral cavity, esophagus, anal canal, distal urethra and vagina, and Urinary epithelium cell; Sensory transducer cells including, but not limited to: Auditory inner hair cell of organ of Corti, Auditory outer hair cell of organ of Corti, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye, Proprioceptive primary sensory neurons, Touch-sensitive primary sensory neurons, Type I carotid body cell, Type II carotid body cell, Type I hair cell of vestibular system of ear, Type II hair cell of vestibular system of ear, and Type I taste bud cell; Autonomic neuron cells including, but not limited to: Cholinergic neural cell, Adrenergic neural cell, and Peptidergic neural cell; Sense organ and peripheral neuron supporting cells including, but not limited to: Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell, and Enteric glial cell; Central nervous system neurons and glial cells including, but not limited to: Astrocyte, Neuron cells, Oligodendrocyte, and Spindle neuron; Lens cells including, but not limited to: Anterior lens epithelial cell, and Crystallin-containing lens fiber cell; Metabolism and storage cells including, but not limited to: Adipocytes, and Liver lipocyte; Barrier function cells including, but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nonciliated cell, Epididymal principal cell, and Epididymal basal cell; Extracellular matrix cells including, but not limited to: Ameloblast epithelial cell, Planum semilunatum epithelial cell of vestibular system of ear, Organ of Corti interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementoblast/cementocyte, Odontoblast/odontocyte, Hyaline cartilage chondrocyte, Fibrocartilage chondrocyte, Elastic cartilage chondrocyte, Osteoblast/osteocyte, Osteoprogenitor cell, Hyalocyte of vitreous body of eye, Stellate cell of perilymphatic space of ear, Hepatic stellate cell, and Pancreatic stelle cell; Contractile cells including, but not limited to: Skeletal muscle cell, Satellite cell, Heart muscle cells, Smooth muscle cell, Myoepithelial cell of iris, and Myoepithelial cell of exocrine glands; Blood and immune system cells including, but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells, and committed progenitors for the blood and immune system; Germ cells including, but not limited to: Oogonium/Oocyte, Spermatid, Spermatocyte, Spermatogonium cell, and Spermatozoon; Nurse cell including, but not limited to: Ovarian follicle cell, and Sertoli cell, Thymus epithelial cell; Interstitial cells including, but not limited to: Interstitial kidney cells and any combination of the foregoing.

Non-limiting examples of other known biologics include, but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-Cide, HumaSPECT, HuMax-CD4, HuMax-EGFr, Humira, HuZAF, Hybri-ceaker, Ilaris, Indimacis-125, Kadcyla, Lemtrada, LeukArrest, LeukoScan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Stelara, Synagis, Tactress, Theracim, Theragyn, Theraloc, Tysabri, Vectibix, Verluma, Xolair, Yervoy, Zenapax, and Zevalin and combinations thereof.

Non-limiting examples of known Monoclonal antibodies include, but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, LBR-101/PF0442g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Luliziumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Nam ilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Tenelixmab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox and combinations thereof.

Examples of vaccines developed for viral diseases include, but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, and Yersinia pestis vaccine; Examples of parasitic diseases include, but are not limited to: Malaria vaccine, Schistosomiasis vaccine, Chagas disease vaccine, Hookworm vaccine, Onchocerciasis river blindness vaccine for humans, Trypanosomiasis vaccine, and Visceral leishmaniasis vaccine; Examples of non-infectious diseases include, but are not limited to: Alzheimer's disease amyloid protein vaccine, Breast cancer vaccine, Ovarian cancer vaccine, Prostate cancer vaccine, and Talimogene laherparepvec (T-VEC); also vaccines including, but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, MenHibrix, Menomune-A/C/WW-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TEN IVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include, but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), Adacel, Adalimumab, Adenoscan (Adenosine Injection), Adenosine Injection (Adenoscan), Adrenaclick, AdreView (lobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX40L, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalam in for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), DepoCyt (Cytarabine Liposome Injection), DepoDur (Morphine Sulfate XR Liposome Injection), Desmopressin Acetate Injection (DDAVP Injection), Depo-Estradiol, Depo-Provera 104 mg/ml, Depo-Provera 150 mg/ml, Depo-Testosterone, Dexrazoxane for Injection, Intravenous Infusion Only (Totect), Dextrose/ Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscarnet Sodium Injection (Foscavir), Foscavir (Foscarnet Sodium Injection), Fosphenytoin Sodium Injection (Cerebyx), Fospropofol Disodium Injection (Lusedra), Fragmin, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), Iobenguane 1123 Injection for Intravenous Use (AdreView), Iopromide Injection (Ultravist), Ioversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5 NS (Potassium Chloride in 5% Dextrose and Sodium Chloride Injection), KCL in D5W, KCL in NS, Kenalog 10 Injection (Triamcinolone Acetonide Injectable Suspension), Kepivance (Paliferm in), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprevv), Omnitarg, Omnitrope (Somatropin [ rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pam idronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGIntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pram lintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Sclerostin Ab, Sensipar (cinacalcet), Sensorcaine (Bupivacaine HCl Injections), Septocaine (Articane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intra-articular Injection), Tarceva, Taxotere (Docetaxel for Injection), Technetium Tc 99m, Telavancin for Injection (Vibativ), Temsirolimus Injection (Torisel), Tenormin I.V. Injection (Atenolol Inj), Teriparatide (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and combinations thereof. It is to be appreciated that mutations of any or all of the drugs and biologics (e.g., antibodies, antisense, RNA interference, gene therapy, primary and embryonic stem cells, and vaccines) set forth above are considered to be within the purview of the invention.

Test Methods

Breaking and Sliding Friction Test

The following procedure was used to evaluate the static and dynamic friction of embodiments of the invention. Each test syringe was attached to a variable pressure pump (Barnant Air Cadet-model 420-3901) by securing a ¼ OD, ⅛ ID silicone tube to its tip (the tip was not fitted with a needle). The stopper assembly with the barrier film was positioned in the syringe to be at the bottom of its motion (closest to the tip). At the beginning of each test, the pressure was slowly adjusted starting at 2 psi and increasing about 1 psi every 30 seconds until syringe stopper movement was initiated (away from tip). The pressure to initiate movement was noted as P break. After the movement was initiated, the pressure was reduced to the lowest level that still allowed sliding. This pressure was noted as P sliding. All pressures were recorded in PSI. The test provided relative data on sliding properties.

Air Leak Test

The same apparatus and setup as described above was then used to evaluate air leakage. The syringe stopper was attached to the pressure pump. However, in this test the stopper was moved to the topmost position within the syringe (farthest from the tip) and the syringe assembly was placed in a 2 Liter glass beaker filled with deionized water. The pressure was set to 3 psi. If no leaks were detected (any sign of visual bubble formation) after 5 minutes, the pressure was increased by 1 psi. This procedure was repeated on each syringe until leaking occurred (or about 15-17 psi when the air was sufficient to eject the syringe stopper from the barrel). The minimum pressure required to cause an observable leak after 5 minutes was recorded in psi. This test was used for evaluating air leakage on Examples 1A, 1B, 1C.

For Examples 1-8 and the comparative example, air leakage was evaluated by performing the test as specified by I.S. EN ISO 7886-1:1998 Annex B, with the following exceptions: i) A bourdon tube gauge was used in place of a manometer, and ii) Deionized water in place of freshly boiled water.

Static and Dynamic Force Test

The test was performed as specified by I.S. EN ISO 7886-1:1998 Annex G, with the following exceptions: i)

Syringe is mounted so that nozzle is pointing down, ii) No liquid was expelled; only air was expelled, and iii) Forces resulting from travel from the total graduated capacity position to 20 mm from that point were recorded.

Static force is defined as the value at the first inflection point in the force versus displacement graph. Dynamic force is the value after 15 mm of travel.

Toluene Exposure Test

Figure 14:
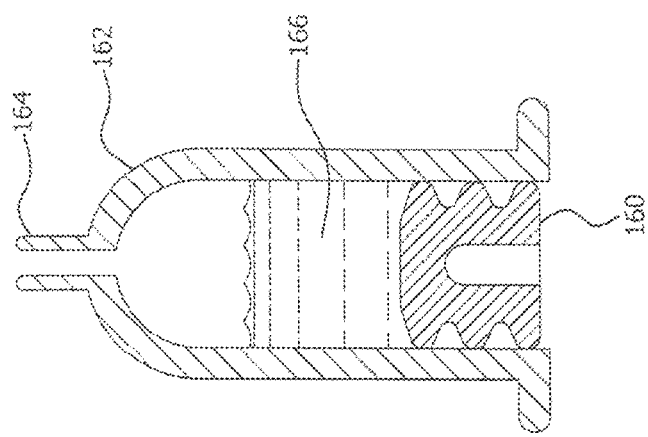
FIG. 14 is a schematic illustration of the test apparatus for accessing the barrier properties of a stopper in accordance with an embodiment.
Figure 16:
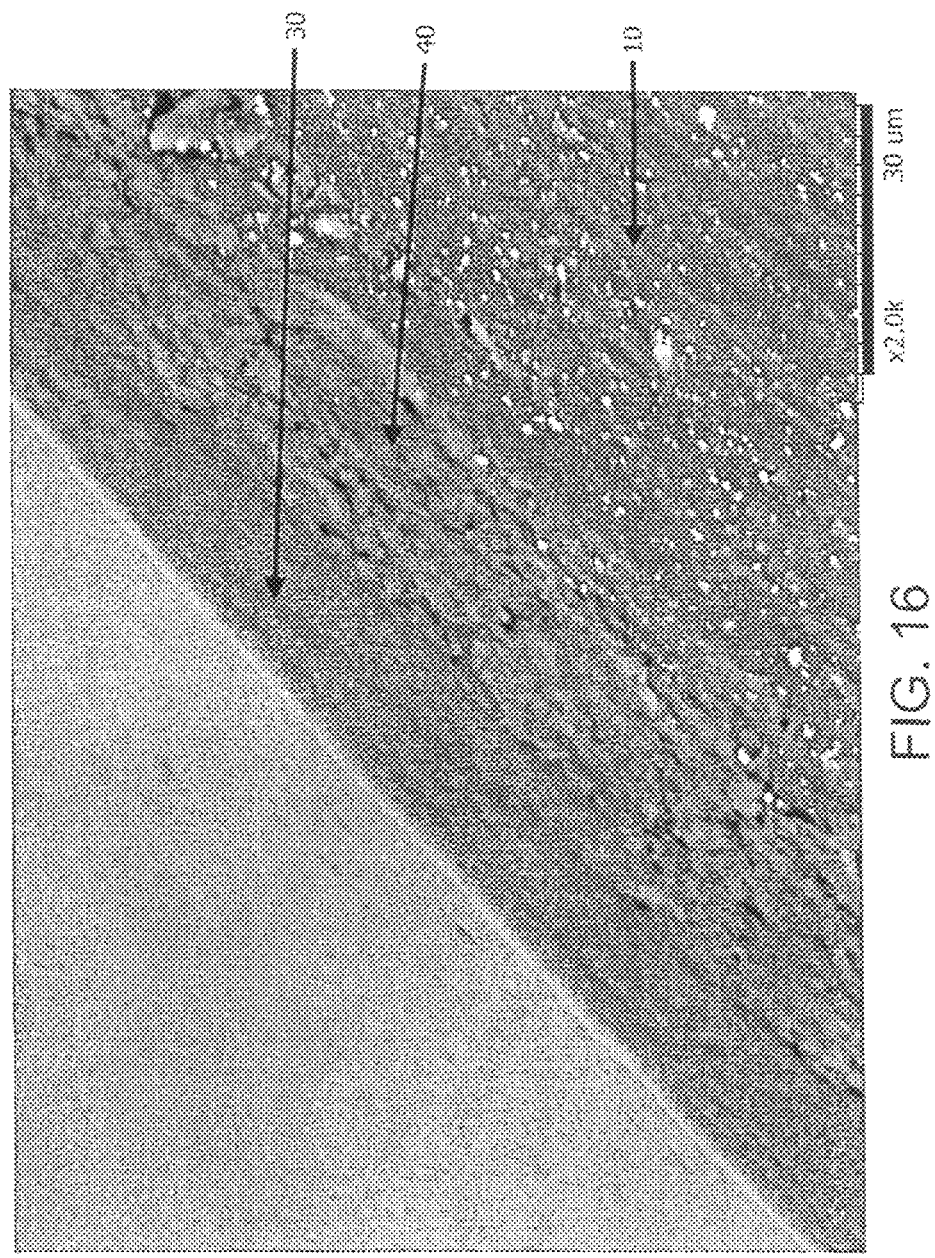
FIG. 16 is a scanning electron micrograph (SEM) showing a cross-section a stopper in accordance with an embodiment.

This test was used to assess the barrier properties of stoppers. A schematic illustration of the test apparatus is shown in FIG. 14. The initial weight of the stopper was measured using a balance. The stopper (160) was loaded into the barrel (162) of a glass syringe. 1 ml of Toluene (166) was introduced into the barrel through the luer port (164). The luer port was sealed using a tip cap. The entire apparatus was left under the lab hood for 5 hours at room temperature. After 5 hours, the Toluene was removed from the barrel using a syringe. The stopper was removed from the barrel using compressed air. Upon removal of the stopper, it was quickly dried using a Kimwipe® and immediately weighed using the balance. Lower the weight gain of the stopper compared to its initial weight, the more effective its function as a barrier. Less than 1 mg weight gain of the stopper may indicate an effective barrier.

Vent Tube Installation Procedure

Figure 15:
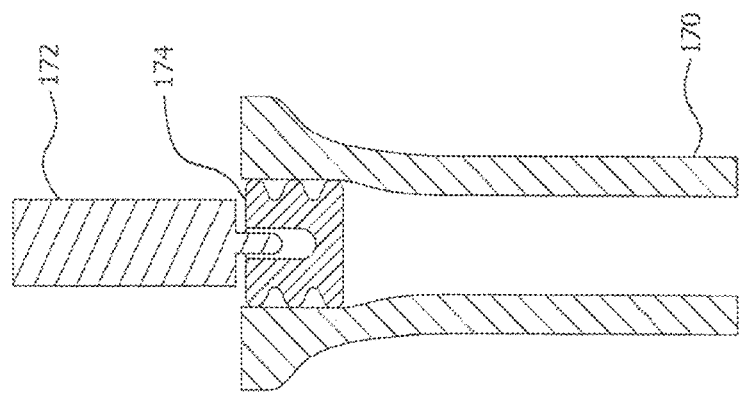
FIG. 15 is a schematic illustration of a test apparatus to determine the durability of a stopper in accordance with an embodiment.

FIG. 15 describes a schematic of the test apparatus comprising a vent tube (170) meant for a 1 mL standard stopper (as specified in ISO11040-5) and a plunger (172). The vent tube, part of a SVH200 Semiautomatic Stoppering Machine from Groninger was used in this procedure. The apparatus was loaded into a universal testing machine capable of moving the plunger at a rate of 0.7 meters/sec. As shown in FIG. 15, the stopper (174) was placed on to the top of the vent tube (170). The test was initiated by moving the plunger at a rate of 0.7 meters/sec to push the stopper through the vent tube. The test was complete when the stopper traversed the entire length of the vent tube.

Tensile, Modulus, Strain to Break

Materials were evaluated for tensile strength, modulus and strain to break according to ATM D882-10 using 0.25 inch by 3 inch samples and a cross head rate of 20 inches/min and one inch gauge length.

EXAMPLES

Example 1A, 1B and 1C

Examples of certain embodiments of the invention were constructed using a single layer of densified ePTFE films as the barrier. The films were obtained by process described in U.S. Pat. No. 7,521,010 to Kennedy, et al. The films had thicknesses of 25 microns, 10 microns, and 5 microns, respectively. Eight commonly available disposable plastic syringe barrels and stoppers with shafts were obtained. Four were 1 ml plastic syringes and four were 3 ml plastic syringes. Each included an elastomer stopper comprising a butyl rubber. The syringes were thoroughly washed with 95% hexane to remove any silicone oil. The washed syringe barrels and stoppers were allowed to dry for 5 days on an air hood to ensure complete evaporation of the hexane. Syringe stoppers were made by taking a densified ePTFE film and applying it to the stopper. Samples were made using these different film thicknesses. The films were first heated by a heat gun (Karl Leister, CH 6056-Hotwind S) set at 600° C. at a distance of about 6-8 inches from the nozzle. The films were then drawn around the stopper in the presence of the heat (thereby using the stopper as a male plug or mold). Care was taken to ensure that the film was adequately heated so that it would readily form without distorting the stopper shape and the heat of the heat gun did not deform the stopper. The four densified ePTFE wrapped stoppers were installed into the silicone free plastic syringe barrels for subsequent testing.

Table 1 below demonstrates the performance as measured by the breaking and sliding friction test and the air leak test of each wrapped stopper compared to a silicone oil control. It can be seen that the thin densified ePTFE films showed better performance than the relatively thicker films with respect to providing an airtight seal. This was in part due to unavoidable wrinkling around the stopper contours in this process.

TABLE 1

| Syringe Type | Film Cover | P break, (psi) | P slide, (psi) | P, min air leak (psi) |
|---|---|---|---|---|
| (1 mL) | Example 1A 1 mil Densified EPTFE | 14 psi | 12 psi | 1 psi |
| | Example 1B 0.4 mil Densified EPTFE | 14 psi | 13 psi | 10 psi |
| | Example 1C 0.2 mil Densified EPTFE | 9 psi | 8 psi | 13-15 psi |
| | None/Silicone Oil | 7 psi | 6 psi | 16-18 psi |
| BD (3 mL) | Example 1A 1 mil Densified EPTFE | 8 psi | 6 psi | 1 psi |
| | Example 1B 0.4 mil Densified EPTFE | 5-6 psi | 3 psi | 1 psi |
| | Example 1C 0.2 mil Densified EPTFE | 5 psi | 3-4 psi | 7 psi |
| | None/Silicone Oil | 4-5 psi | 2-3 psi | >20 psi |

Other embodiments of the present invention were constructed using a process of thermoforming a barrier preform and molding an elastomer material within the form to construct a syringe stopper.

Example 2

A barrier was created from a single densified ePTFE film 1.7-1.8 mil thick, which was obtained by the process described in U.S. Pat. No. 7,521,010 to Kennedy, et al. The film (104) was placed in the thermoforming equipment as depicted in FIG. 1 using the mold depicted in FIGS. 2A and 2B. The thermoforming equipment (100) uses hot air to heat the mold (200), and the pressure drop through the apparatus supplies the force to form the material. The mold has round cavities (202a-d) having different dimensions. One of 0.380 inches, one of 0.372 inches, one of 0.365 inches, and one of 0.358 inches. The bottom portion of the cavities have a rounded corner (203) with a radius of 0.079 inches, a side straight wall 205 of 0.188 inch height, and contain a 0.201 inch wide, 2 micron porous stainless steel disc (204) at its bottom most point.

At room temperature a pressure of 5 psi was applied. The heater on the hot air system (102) (Osram Sylvania 6000W, 240V, 25A) was activated using a set point of 385° C. as measured by the thermocouple (106) above the mold. Once a temperature of 360° C. was reached below the mold cavities, as measured by the bottom thermocouple (108), the system was held for 5 minutes. Pressure was then increased by increasing the inlet air flow using the hot air system inlet valve (110). The pressure was increased at a rate of approximately 3 psi/minute from 5 psi to 13 psi. Above 13 psi, the pressure was increased at approximately 1 psi/minute up to 18 psi. This pressure was sufficient to form the densified ePTFE sheet. The sample was held at this pressure for 5 minutes, and then the heater was deactivated allowing the mold and film to cool. The mold was allowed to cool to below 50° C., as measured by the bottom thermocouple, before removing the sample. Any technique suitable for heating both the material and the mold as well as adding the air pressure to form the material will suffice. For example the mold may be simply bolted together and placed in an oven or heated press with an air line to supply the pressure. Other processes known for thermoforming, bladder forming or vacuum forming may also be used.

Figure 3:
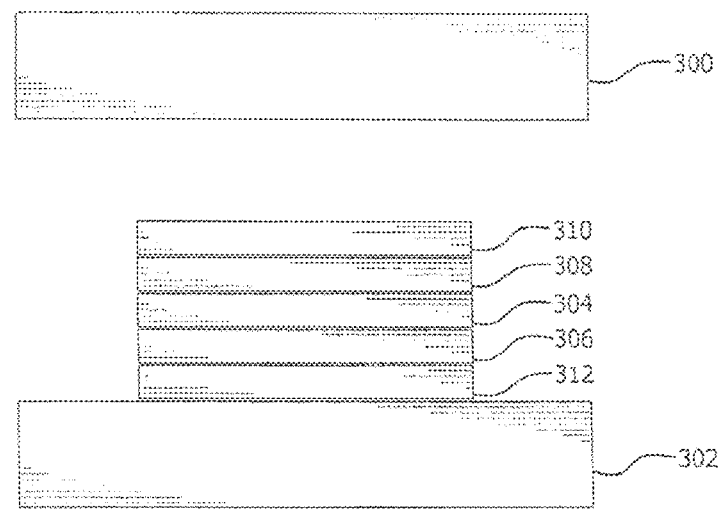
FIG. 3 is a schematic illustration of a lay-up in the press for compression molding in accordance with at least one embodiment.

To coat the inside of the barrier with an elastomer solution, sample cavities were filled with a 10% by weight solution of the elastomer in MEK and allowed enough time to dry so that a substantial amount of the solvent was evaporated. Each cavity was loaded with 1-1.5 grams of elastomer (Viton GF-600S from DuPont compounded with varox D8PH and Diak 7 and processed to a crumb 304 by Eagle Elastomer Inc., Cuyahoga Falls, Ohio). The mold 306 along with the above thermoformed densified ePTFE sheet was loaded into a press with both platens 300, 302 preheated to 100° C. As represented in FIG. 3, a 10 mil Aluminum sheet 312 was placed on the lower platen 302. A Kapton sheet (308) and a steel caul plate 310 were placed below the upper press platen (300) to provide uniform pressure. The sample was heated under no pressure for 45 minutes, and then compressed under a force of 8000 lbs. The platens were slowly closed and temperature based set points were used in the following press cycle:

Step 1: Close platens
Step 2: Heat for 10 minutes at 100° C.
Step 3: 5 minutes at 120° C.
Step 4: 15 minutes at 175° C.
Step 5: 1 minute at 30° C.
Step 6: Open platens Samples were then cut from the release sheet using a razor blade, affixed to a stopper rod using an acrylic adhesive (3M Scotch-Weld Structural Adhesive DP-8005) and installed within a standard 1 cc glass syringe barrel free of silicone oil, and tested.

Example 3

A sample was prepared in a manner similar to Example 2 except that the densified ePTFE barrier was formed to shape using a faster pressure ramp rate. The procedure of Example 2 was followed except that a pressure ramp rate of approximately 3 psi/minute from 5 psi to 18 psi was chosen. This ramp rate was obtained by closing only the exit air valve (112). This molding procedure resulted in a barrier film with milky appearance, which may indicate that there was some porosity induced in the material by the speed of the forming process.

The mold cavity was then filled with elastomer, molded and attached to a syringe stopper according to the process described in Example 2. After insertion into a glass syringe barrel the sample was tested.

Example 4

A sample was prepared in a manner similar to that described in Example 2, except that one surface of the densified ePTFE barrier material was textured before it was thermoformed. One side of the densified ePTFE material was deformed using a coarse glass bead sandblaster. The sandblaster nozzle was set to 15 psi and held approximately 9 inches away from the sample, which was affixed to a cardboard backer. The sandblaster was passed 5 times over the entire surface of the sample. This process resulted in significant mechanical deformation on one side of the film which increased the apparent surface roughness.

The barrier material was placed in the mold with the roughened side up so that it would be oriented towards the elastomer. The mold cavity was then filled with elastomer, molded and attached to a syringe stopper according to the process described in Example 2. After insertion into a glass syringe barrel, the sample was tested.

Example 5

A sample was prepared similar to Example 1 except that the densified ePTFE barrier material exposed to a plasma treatment after thermoforming. The material was left in the mold and placed in a plasma vacuum chamber with a 90/10 mix of He/H2 and an exposure time of 10 minutes. This sample was not coated with an elastomer solution before compression molding. Otherwise the procedures of Example 2 were followed.

The mold cavity was then filled with elastomer, molded and attached to a syringe stopper.

Example 6

A sample was prepared in a manner similar to Example 2, except that an ePTFE/PFA composite film was used as a barrier. The barrier was obtained in a manner similar to that described in Example 2 of WO 94/13469 to Bacino. The resulting barrier is an ePTFE material with PFA on one of its side surfaces. The barrier material was placed in the mold with the PFA side of the composite facing upwards, such that after thermoforming the PFA would be oriented towards the inside of the mold. The thermoforming process followed that of Example 2 except that the heater set point was 295° C. and the mold cavity set point was approximately 275° C. Moreover, the pressure ramp rate in the molding process was approximately 11.5 psi/min from 5 to 18 psi. The composite material was held at 18 psi for approximately 15 seconds before cooling. After the sample was removed from the mold it was inverted so that the ePTFE layer was facing inward.

Example 7

A sample was prepared in a manner similar to Example 2 except that the barrier was an ePTFE/densified ePTFE composite. The barrier was prepared according to the methods disclosed in U.S. Pat. No. 6,030,694 to Dolan. The material was oriented in the mold with the ePTFE side of the composite downward, the molded sample was inverted after thermoforming so that the ePTFE layer was facing inward. In this example the mold that was used had the same mold cavities of diameters identical to those of Example 2 ("A"=0.380 inches, "B"=0.372 inches, "C"=0.365 inches, "D"=0.358 inches.) However, each cavity was a straight cylinder of 0.252 inch height and had a stainless steel porous disc making up the bottom of the cavity.

Example 8

Figure 4:
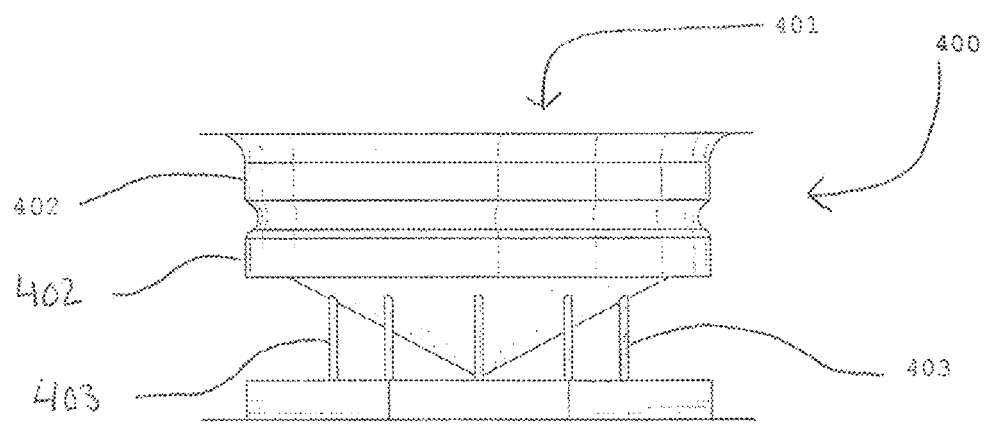
FIG. 4 is a schematic illustration of the a single cavity mold used to make the stopper described in Example 8 in accordance with at least one embodiment.

An ePTFE/FEP composite barrier was constructed using the procedure described in Bacino (WO 94/13469). In this example, rather than thermoforming, the composite barrier was placed over a mold cavity and was formed by compression molding. A single cavity mold 400 was used having a profile generally depicted in FIG. 4. The mold 400 included a cavity 401 and ribs 402. Vent holes 403 permitted air to escape during the molding process. It is to be noted that the mold 400 depicted in FIG. 4 is one example of mold that can be used in the location of mold 306, as is depicted in FIG. 3. The mold 400 had a primary diameter of 0.49 inches.

Example 9

A layer of FEP about 0.5 mils in thickness (FEP 100, DuPont) was laminated to a layer of densified expanded PTFE film [Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse)]. The two layers were stacked on top of each other in a pin frame and heating to 380° C. in an oven for 15 minutes. A layer of porous expanded PTFE [thickness: 27.5 micrometers, matrix tensile strength: 66.8 MPa (longitudinal), 75.8 MPa (transverse), strain to break: 131% (longitudinal), 91% (transverse), bubble point: 22.6 psi] was placed on the densified ePTFE-FEP laminate such that the porous expanded PTFE layer faced the FEP layer in the laminate. These three layers were placed between two smooth metal plates, the plates were clamped to a clamping pressure of about 1 psi. The plates were then placed in an oven at 305° C. for 15 minutes. The resulting three layer composite material (densified ePTFE-FEP-porous ePTFE) was then cooled to about 40° C.

This composite material was then thermoformed using heat and vacuum to create a pre-form. The pre-form was constructed by heating the composite to a sufficiently high temperature and then drawing the composite over a male plug using differential pressure. The composite material was loaded into the thermoforming apparatus such that the densified ePTFE layer faced the plug. The composite was heated using a hot air gun (Steinel HG2310) with air exit temperature of 380° C. by placing the gun about 5 mm away from the surface of the composite. After 5 seconds, the film was subjected to a vacuum of −85 kPa. The composite was continued to be heated for another 15 seconds and cooled to about 40° C. under vacuum.

The resulting pre-form sample was then inverted and then placed into a rubber molding cavity charged with 3.5 grams of elastomer (50 Durometer halobutyl rubber), and the stopper was formed by compression molding. The mold was built to geometry specified for 1 mL standard plunger per the ISO standard ISO11040-5:2001(E), with an additional 5% shrinkage factor incorporated.

The cavity was loaded in a press with both platens preheated to 120° C. The platens were closed to 55,500 lbs (about 8700 psi total internal pressure). The platens were then heated at 180° C. for 5 minutes and then cooled under pressure to 40° C. The pressure was released and the stopper was ejected. The resulting stopper was washed using a detergent and triple rinsed with de-ionized water. Stopper samples were then cut from the release sheet using a razor blade. They were subjected to two 30 minute cycles in an autoclave at 121° C. The static and dynamic force on the stopper was measured to be 2.5 N and 2.1 N respectively. The weight gain of the stopper after the Toluene Exposure test was 0 mg, indicating that the stopper functioned as an effective barrier. Further, the same stopper was subjected to the vent tube placement test and then the Toluene exposure test was repeated. The weight gain was still 0 mg, indicative of superior barrier function of the stopper. The stopper was also tested for leaks using the air leak test and no leak was detected. The areal transformation (%) was calculated to be 82%.

Example 10

A layer of EFEP about 2.7 microns thick (RP-4020, Daikin) was laminated to a layer of densified expanded PTFE film in a manner similar to the one described below. The densified expanded PTFE film had the following properties: Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse). The two layers were stacked on top of each other in a pin frame and heated to 380° C. in an oven for 15 minutes. The resulting two-layer composite barrier (EFEP—densified expanded PTFE) was then cooled to about 40° C.

This composite barrier was then thermoformed using heat and vacuum to create a pre-form. The pre-form was constructed by heating the composite to a sufficiently high temperature to draw the composite over a male plug using differential pressure. The mold consisted of a flat plate with a 60 mm diameter woven fiberglass mat placed over an opening in the center which had a 4.8 mm recess. The male plug was a 12.7 mm diameter pin 25.4 mm in height, and was placed in the center of the mold.

The composite barrier was loaded into the thermoforming apparatus such that the densified ePTFE layer faced the plug. The composite barrier was heated using a hot air gun (Steinel HG2310) with air exit temperature of 380° C. by placing the gun about 5 mm from the surface of the composite barrier. After heating for 5 seconds, the film was subjected to a vacuum of −85 kPa. The composite barrier was heated for another 15 seconds and cooled to about 40° C. while under vacuum.

An aluminum female mold which had a cavity of a geometry to match the thermoforming pin was prepared by heating to 280° C. The mold cavity matched the geometry of the plug with 1.6 mm clearance on all sides. EFEP (RP-4020, from Daikin) resin was provided to the mold. The thermoforming pin, with the pre-form on it, was also heated to 205° C. and inserted into the mold cavity. The entire assembly was cooled to 25° C. After cooling, the molded assembly was removed, providing a container with a wall thickness of approximately 1.6 mm and a PTFE based barrier on the interior of the container. The areal transformation (%) was calculated to be 68%.

Example 11

Figure 17B:
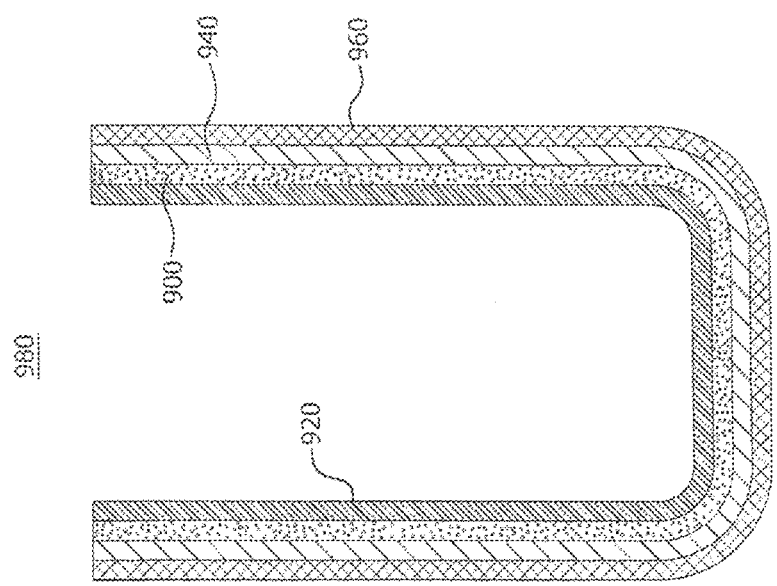
FIG. 17B is a schematic illustration of a cross-sectional view of the container formed in Example 11.
Figure 17A:
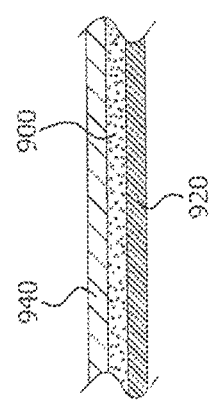
FIG. 17A is a schematic illustration of a portion of the container formed in Example 11.

Reference is made to FIGS. 17A and 17B in the following example. A layer of FEP (900) about 0.5 mils in thickness (FEP 100, DuPont) was laminated to a layer of densified expanded PTFE (920) in a manner similar to the one described below. The densified expanded PTFE film had the following properties: Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse). The two layers were stacked on top of each other in a pin frame and heated to 380° C. in an oven for 15 minutes.

Next, a layer of porous expanded PTFE (940) was placed on the densified ePTFE-FEP laminate such that the porous expanded PTFE layer faced the FEP layer in the laminate. The porous expanded PTFE membrane had the following properties: Thickness—27.5 micrometers; Matrix Tensile Strength—66.8 MPa (longitudinal), 75.8 MPa (transverse); Strain to Break—131% (longitudinal), 91% (transverse); Bubble Point—22.6 psi. These three layers were placed between two smooth metal plates, the plates were clamped to a clamping pressure of about 1 psi. The plates were then placed in an oven at 305° C. for 15 minutes. The resulting three-layer composite material was then cooled to about 40° C.

The three-layer composite material (shown in FIG. 17A) was then thermoformed in combination with an additional layer (960) of 10 mil thick Kynar®2800 PVDF, hand laid in contact with the porous ePTFE side of the composite. Heat and vacuum were used to create a pre-form. The pre-form was constructed by heating the composite to a sufficiently high temperature to draw the composite over a male plug mold using differential pressure. The three-layer composite material with the additional PVDF layer was loaded into the thermoforming apparatus such that the densified ePTFE (920) layer faced the plug. The mold consisted of a 60 mm sintered stainless steel plate with a 8.3 mm lip on the outer edge and the plug located in the center. The plug was made of stainless steel and had a diameter of 15.9 mm and a height of 15.9 mm.

The composite with the additional PVDF layer was heated using a hot air gun (Steinel HG2310) with air exit temperature of 380° C. by placing the gun about 5 mm away from the surface of the composite. After heating for 5 seconds, the film was subjected to a vacuum of −85 kPa. The composite with the additional PVDF layer was heated for another 15 seconds and cooled to about 40° C. while under vacuum.

The resulting article (980) was shaped in the form of a container and shown in FIG. 17B. The areal transformation (%) was calculated to be 118%.

Comparative Example

Commercial siliconized butyl stopper made for 1 cc single dose glass pre-filled syringe.

TABLE 2

| Sample | Material | Cavity | Static Force (grams) | Dynamic Force (grams) | Leak pressure (kPa) |
|---|---|---|---|---|---|
| Example 2 | Densified ePTFE | A | 1517.2 | 1232.7 | Pass |
| | | C | 583.5 | 558.1 | Pass |
| | | D | 358.4 | 287.1 | −88 |
| Example 3 | Low porosity ePTFE | A | 1528.4 | 1511.2 | Pass |
| | | B | 915.3 | 880.9 | Pass |
| | | C | 621.8 | 735.6 | Pass |
| | | D | 418.6 | 418.5 | −88 |
| Example 4 | Mechanically deformed | A | 979.7 | 777.5 | Pass |
| | | B | 734.1 | 612.3 | Pass |

TABLE 2-continued

| Sample | Material | Cavity | Static Force (grams) | Dynamic Force (grams) | Leak pressure (kPa) |
|---|---|---|---|---|---|
| | densified ePTFE | C | 705.5 | 655.5 | Pass |
| | | D | 665.9 | 478.6 | Pass |
| | | B | 1769.2 | 1635.4 | Pass |
| | | C | 844.0 | 638.5 | Pass |
| | | D | 574.6 | 415.3 | −88 |
| Example 6 | ePTFE/PFA composite | A | 2683.8 | 1991.0 | Pass |
| | | B | 2244.4 | 1790.8 | Pass |
| | | C | 1675.3 | 1291.0 | Pass |
| Comparative Example | Butyl + silicone oil | n/a | 750.5 | 323.7 | Pass |

What is claimed is:

1. A pre-filled syringe comprising:
   a silicone free syringe barrel having a first end and a second end;
   an elastomeric stopper comprising an elastomer, the elastomeric stopper being positioned within the syringe barrel, creating a volume for containment of at least one therapeutic;
   an expanded polytetrafluoroethylene film having a first side and a second side,
   wherein the elastomer is at least partially imbibed into the first side of the expanded polytetrafluoroethylene film.

2. The pre-filled syringe of claim 1, further comprising a needle attached to the first end of said barrel.

3. The pre-filled syringe of claim 1, wherein said therapeutic comprises at least one bioactive selected from coagulation factors, cytokines, epigenetic protein families, growth factors, hormones, peptides, signal transduction molecules, vaccines, and combinations thereof.

4. The pre-filled syringe of claim 1, wherein said therapeutic comprises at least one bioactive selected from antibodies, antisense, RNA interference, target receptors, and combinations thereof.

5. The prefilled syringe of claim 4, wherein the therapeutic is anti-ngf.

6. The pre-filled syringe of claim 1, wherein said therapeutic comprises mutations of a bioactive selected from coagulation factors, cytokines, epigenetic protein families, growth factors, hormones, peptides, signal transduction molecules, vaccines, and combinations thereof.

7. The prefilled syringe of claim 1, wherein said therapeutic comprises at least one bioactive selected from protein kinases, esterases, phosphatases, ion channels, proteases, structural proteins, membrane transport proteins, nuclear hormone receptors, and mutations and combinations thereof.

8. The prefilled syringe of claim 1, wherein said therapeutic comprises at least one bioactive selected from antibodies, antisense, RNA interference, target receptors, and combinations thereof.

9. The prefilled syringe of claim 1, wherein said therapeutic comprises at least one bioactive selected from primary and embryonic stem cells.

10. The prefilled syringe of claim 1, wherein the therapeutic is factor VII.

11. The pre-filled syringe of claim 1, wherein the therapeutics is used for treatment of ocular disease.

* * * * *